United States Patent
Pressacco

(10) Patent No.: US 9,949,834 B2
(45) Date of Patent: Apr. 24, 2018

(54) PROSTHETIC ELEMENT FOR BONE EXTREMITIES SUCH AS FINGERS OR TOES, OR FOR TEETH, AND CORRESPONDING PRODUCTION METHOD

(71) Applicant: LIMACORPORATE SPA, San Daniele del Friuli (IT)

(72) Inventor: Michele Pressacco, Udine (IT)

(73) Assignee: LIMACORPORATE SPA, San Daniele del Friuli (IT)

( * ) Notice: Subject to any disclaimer, the term of this patent is extended or adjusted under 35 U.S.C. 154(b) by 277 days.

(21) Appl. No.: 14/390,989

(22) PCT Filed: Apr. 8, 2013

(86) PCT No.: PCT/IB2013/000618
§ 371 (c)(1),
(2) Date: Oct. 6, 2014

(87) PCT Pub. No.: WO2013/150369
PCT Pub. Date: Oct. 10, 2013

(65) Prior Publication Data
US 2015/0118650 A1    Apr. 30, 2015

(30) Foreign Application Priority Data
Apr. 6, 2012  (IT) .............................. UD2012A0059

(51) Int. Cl.
*A61C 8/00*  (2006.01)
*A61F 2/30*  (2006.01)
(Continued)

(52) U.S. Cl.
CPC ........ *A61F 2/30767* (2013.01); *A61C 8/0037* (2013.01); *A61C 8/0075* (2013.01);
(Continued)

(58) Field of Classification Search
CPC .. A61F 2/30767; A61F 2/3094; A61F 2/4225; A61F 2/4241; A61F 2/30771;
(Continued)

(56) References Cited

U.S. PATENT DOCUMENTS 3,852,045 A * 12/1974 Wheeler ................... A61F 2/28
  419/2
3,855,638 A * 12/1974 Pilliar ................... C23C 24/087
  433/173
(Continued)

FOREIGN PATENT DOCUMENTS

DE  20 2004 013500 U1  1/2006
EP       1 381 172 A2  1/2004
(Continued)

OTHER PUBLICATIONS

Search Report for PCT/IB2013/000618 dated Jul. 16, 2013.
(Continued)

*Primary Examiner* — Stephen R Crow
*Assistant Examiner* — Garrett Atkinson
(74) *Attorney, Agent, or Firm* — Marshall, Gerstein & Borun LLP

(57) ABSTRACT

Prosthetic element for bone extremities such as fingers or toes, or teeth, comprising a trabecular part (20, 40, 120) and two end parts or stumps (12, 34, 112; 15, 39, 115).

11 Claims, 4 Drawing Sheets

(51) Int. Cl.
*A61F 2/42* (2006.01)
*B22F 3/105* (2006.01)
*B22F 3/11* (2006.01)
*B33Y 10/00* (2015.01)
*B33Y 80/00* (2015.01)

(52) U.S. Cl.
CPC ........ *A61F 2/3094* (2013.01); *A61F 2/30771* (2013.01); *A61F 2/4225* (2013.01); *A61F 2/4241* (2013.01); *B22F 3/1055* (2013.01); *B22F 3/1103* (2013.01); *A61C 2008/0046* (2013.01); *A61F 2002/30011* (2013.01); *A61F 2002/3092* (2013.01); *A61F 2002/3093* (2013.01); *A61F 2002/3097* (2013.01); *A61F 2002/30331* (2013.01); *A61F 2002/30649* (2013.01); *A61F 2002/30909* (2013.01); *A61F 2002/30968* (2013.01); *A61F 2002/30985* (2013.01); *B22F 2003/1051* (2013.01); *B33Y 10/00* (2014.12); *B33Y 80/00* (2014.12)

(58) Field of Classification Search
CPC .. A61F 2002/30649; A61F 2002/30011; A61F 2002/3093; A61F 2002/30331; A61F 2002/3092; A61F 2002/30985; A61F 2002/30968; A61F 2002/3097; A61F 2002/30909; B22F 3/1103; B22F 3/1055; B22F 2003/10; A61C 8/0075; A61C 8/0037; B33Y 10/00; B33Y 80/00
USPC ...... 433/167, 191–195, 201.1, 218–223, 225
See application file for complete search history.

(56) References Cited

U.S. PATENT DOCUMENTS

| | | | | |
|---|---|---|---|---|
| 4,011,602 A * | 3/1977 | Rybicki | ................ | A61F 2/3662 433/173 |
| 4,216,548 A * | 8/1980 | Kraus | ................ | A61B 17/58 433/173 |
| 4,365,359 A * | 12/1982 | Raab | ................ | A61F 2/30767 427/2.26 |
| 4,406,023 A * | 9/1983 | Harris | ................ | A61F 2/30767 623/10 |
| 4,871,369 A * | 10/1989 | Muller | ................ | A61F 2/3662 623/23.35 |
| 4,872,840 A * | 10/1989 | Bori | ................ | A61C 3/16 433/173 |
| 5,080,672 A * | 1/1992 | Bellis | ................ | A61F 2/30767 419/2 |
| 5,108,443 A * | 4/1992 | Branemark | ................ | A61F 2/3662 606/60 |
| 5,360,448 A * | 11/1994 | Thramann | ................ | A61B 17/863 411/412 |
| 5,534,033 A * | 7/1996 | Simpson | ................ | A61F 2/30721 623/13.14 |
| 5,639,402 A * | 6/1997 | Barlow | ................ | A61F 2/28 264/430 |
| 6,183,515 B1 * | 2/2001 | Barlow | ................ | A61F 2/28 264/497 |
| 6,386,877 B1 * | 5/2002 | Sutter | ................ | A61C 8/0018 433/173 |
| 6,540,784 B2 * | 4/2003 | Barlow | ................ | A61F 2/28 623/16.11 |
| 6,626,950 B2 * | 9/2003 | Brown | ................ | A61F 2/30749 623/23.72 |
| 6,790,233 B2 * | 9/2004 | Brodke | ................ | A61F 2/30767 623/17.11 |
| 7,368,065 B2 * | 5/2008 | Yang | ................ | A61L 27/047 216/103 |
| 7,469,165 B2 * | 12/2008 | Mataya | ................ | B22C 9/00 361/234 |
| 7,901,462 B2 * | 3/2011 | Yang | ................ | A61C 8/0012 623/23.76 |
| 7,998,523 B2 * | 8/2011 | Lerf | ................ | A61L 27/306 228/193 |
| 8,066,770 B2 * | 11/2011 | Rivard | ................ | A61F 2/30767 623/16.11 |
| 8,337,440 B2 * | 12/2012 | Cornacchio | ................ | A61F 5/01 602/19 |
| 8,361,161 B2 * | 1/2013 | Buma | ................ | A61L 27/04 623/22.11 |
| 8,556,972 B2 * | 10/2013 | Gordon | ................ | A61F 2/28 623/16.11 |
| 8,864,826 B2 * | 10/2014 | Pressacco | ................ | A61F 2/30 623/11.11 |
| 9,011,537 B2 * | 4/2015 | Wei | ................ | A61F 2/30 623/16.11 |
| 9,433,480 B2 * | 9/2016 | Pelote | ................ | A61C 8/00 |
| 2005/0112397 A1 * | 5/2005 | Rolfe | ................ | A61B 17/8605 428/593 |
| 2005/0234560 A1 * | 10/2005 | Serbousek | ................ | A61F 2/367 623/23.24 |
| 2007/0073295 A1 * | 3/2007 | Biedermann | ................ | A61B 17/68 606/62 |
| 2010/0003640 A1 * | 1/2010 | Damstra | ................ | A61C 8/0012 433/201.1 |

FOREIGN PATENT DOCUMENTS

| | | |
|---|---|---|
| EP | 1 438 937 A1 | 7/2004 |
| EP | 2 164 428 A2 | 3/2010 |
| WO | WO-03/043543 A1 | 5/2003 |
| WO | WO-2006/099886 A1 | 9/2006 |
| WO | WO-2006/12030 A1 | 11/2006 |
| WO | WO-2008/146141 | 12/2008 |
| WO | WO-2011/138646 A1 | 11/2011 |

OTHER PUBLICATIONS

Written Opinion for PCT/IB2013/000618 dated Jul. 16, 2013.
Collins et al., "Zimmer® Trabecular Metal™ Dental Implant Research: A Brief Overview," Zimmer Dental, 2011.

* cited by examiner

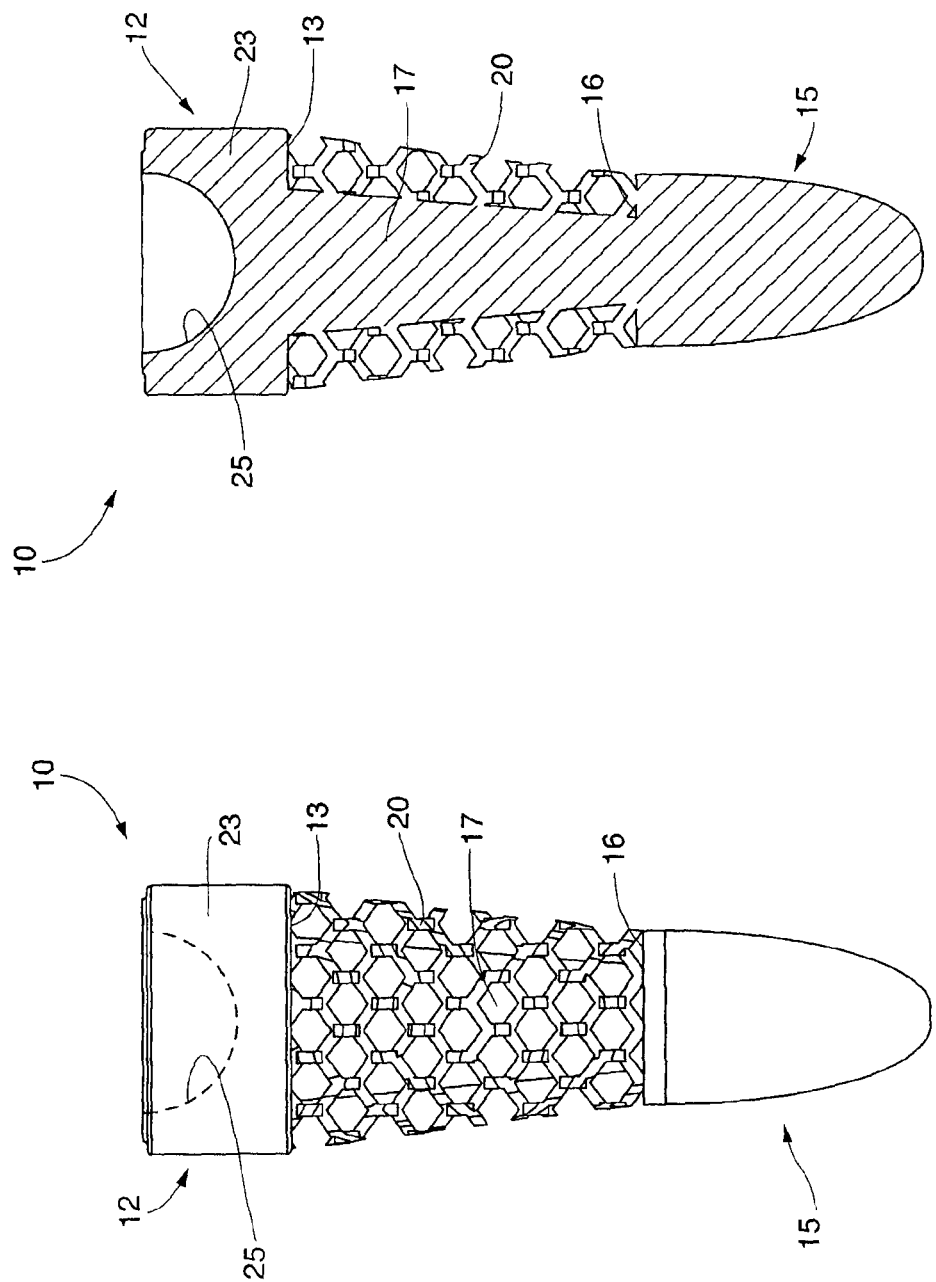

PROSTHETIC ELEMENT FOR BONE EXTREMITIES SUCH AS FINGERS OR TOES, OR FOR TEETH, AND CORRESPONDING PRODUCTION METHOD

FIELD OF THE INVENTION

The present invention concerns a prosthetic element with a cellular structure, preferably used, but not only, in the reconstruction of small joints, such as for example those of a hand or a foot, or for dental implants.

The present invention also concerns the corresponding production method of the prosthetic element.

BACKGROUND OF THE INVENTION

Prosthetic elements are known, which are applied in many parts of the human body, such as for example the knees, shoulders or femoral extremities.

A prosthetic element is known, for example from EP-A-2164428 in the name of the present Applicant, with a cellular structure usable as an acetabulum cup for a femoral prosthesis in implant operations in the acetabulum of the pelvis. The prosthetic element, in this case, has the function of housing a prosthetic head, or an insert, for the acetabulum cup, into which in turn a femoral prosthesis is inserted. The prosthetic element comprises a cap of metal material, the body of which comprises a three-dimensional lattice, trabecular shaped, with a predefined and desired thickness. The lattice is formed by a plurality of open and communicating cavities, which are connected both toward the inside and toward the outside of the cap.

A prosthetic element is also known from WO 2011/138646, also in the name of the present Applicant, which can be used for bone implant operations, such as for example femoral, shoulder or knee prostheses. The prosthetic element in this case comprises a metal support and an insert made of plastic material. The metal support in its turn comprises a first surface, to which said plastic insert is coupled, and a second surface to which the bone part on which the prosthesis is fitted is intended to be coupled. The first surface comprises cavities or holes, suitable to anchor and make solid the plastic material which forms the insert, while the second surface comprises a porous layer of a trabecular shape suitable to optimize the anchoring of the bone. The cited first and second surface are separated by a compact layer, having the function of stopping the plastic material in the injection step for the formation of the plastic insert.

However, in many cases prostheses are required to be applied in bone parts that have very much smaller sizes compared to those cited above, such as for example in the reconstruction of small joints, like those of a hand or a foot, or in the case of dental implants.

The solutions cited above are not suitable for such applications, for example because of the inadequate size of the pores of the porous layer of a trabecular shape.

Some solutions in the state of the art have tackled these problems.

For example, from document EP 1.438.937 a transcutaneous prosthetic element is known, used to recover the functions of partially amputated fingers. The prosthetic element consists of an extracorporeal part, able to substitute the missing end of a finger, and an intracorporeal part consisting of a hollow tubular rod, preferably made of bio-compatible material. The tubular rod is externally lined, for a portion thereof, by a porous layer with three-dimensional meshes, of a not precisely defined shape, for bone integration.

An apparatus for the reconstruction of a metatarsus-phalanx joint is also known from WO 2006/099886.

This apparatus, preferably made of bio-compatible metal, is formed by a part shaped like a concave capsule facing toward the joint, once the apparatus is implanted, and by a rod which instead is inserted in the phalanges. A portion of surface conformed as a net with an open three-dimensional mesh is provided on the rod and inside the concave part.

One disadvantage of these embodiments is that the porous structures of the surfaces for the bone integration, because of the geometry of the meshes, entail a difficult and uneven bone integration.

Another disadvantage of these embodiments is that the shape of the part of the prosthetic element to be inserted into the bony extremity is not optimal for anchorage.

Another disadvantage is the lack of structural continuity between internal rod and external trabecular part.

An intraosseous implant is also known from DE 202004013500U1, for the reconstruction of a tooth, suitable for insertion in the jaw bone, equipped with a covering structure obtained by sintering titanium balls on the external surface of a support rod From the article by Collins, M et al, "Zimmer Trabecular Metal Dental Implant Research: A Brief Overview", a dental implant is also known, having an external layer of trabecular metal in tantalum which covers a structure of titanium alloy. The trabecular metal is formed by applying the tantalum on a substrate of vitreous carbon through a chemical process of deposition through steam.

One disadvantage of these embodiments is that the porous structure is integrated only in a step after the formation of the other structures of the prosthetic elements, and therefore do not allow to overcome limitations of a structural type deriving from the physical and mechanical discontinuity between the different parts which make up the prosthetic element.

Moreover, the production processes needed to make these elements are rather complex, require a long time, are difficult to standardize and produce results that are often dissimilar and not always effective.

One purpose of the present invention is therefore to obtain a prosthetic element with a trabecular structure intended for bone integration in the case of reconstruction of small joints, such as for example those of a hand or foot, and for dental implants, which has higher structural and mechanical characteristics and a higher capacity of bone integration.

Another purpose is to perfect a method to make said prosthetic element, suitable to be used in the reconstruction of small joints and dental implants.

It is another purpose of the present invention to obtain both a trabecular structure with an external conformation which allows the best adhesion and integration possible of the bone, and also an overall shape which guarantees an efficient anchorage, of both the extremities and the central body, to the bone and tissue structures of the patient.

It is also a purpose of the present invention to make a prosthetic element which has a trabecular structure with improved mechanical properties, which allows a uniform bone integration and can be obtained with a highly standardized and repeatable process with great efficiency and conformity of the results.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, a prosthetic element according to the present invention can be used for dental implants or for implants for the bone extremities in the case of reconstruction of small joints, such as for example those of the phalanges of a hand or foot.

The prosthetic element of the present invention comprises a trabecular part, intended for bone integration subsequent to a reconstruction operation undergone by the patient.

According to one characteristic of the present invention, the prosthetic element comprises two end parts, or stumps, connected to each other by a core with a structural function and consisting of a solid body: the stumps may possibly be used not only for their functional use when the prosthetic element is applied to the patient, but also for gripping in the machine during the production step of the prosthetic element itself. Between the stumps a trabecular part is interposed, suitable for bone integration.

According to a first characteristic feature of the present invention, the trabecular part is made at the same time as and externally to the internal core, so as to define, at least partly and in a single body, the external geometry thereof, so as to form an external covering around the core, for example of a circular or quadrangular shape.

Core, trabecular part and stumps therefore make up a structurally continuous finished element, in which all the elements which make up the prosthetic element are obtained substantially in a single body and substantially in the same continuous production step.

One characteristic of the present invention is therefore that the internal core and external trabecular structure are achieved by means of a continuous process of progressive and sequential shaping of the same base material, to define an element that is structurally and mechanically continuous in itself, whose morphology is modified in the production step, for example from the inside to the outside, or from the center to the periphery, according to dimensional parameters that are pre-ordained or defined on each occasion.

In the case of reconstruction of small joints, one of the two stumps, called coupling stump, is shaped so as to define at least a seating to articulate the finger of a hand or toe of a foot, and can assume different shapes, such as for example a cylinder shape.

According to some non-restrictive variants, the coupling stump, corresponding to the seating for the joint, can assume the shape of a parallelepiped, or again a truncated cone, depending on requirements and on the position of the body where the prosthetic element is to be disposed.

According to a variant, an additional element to the coupling stump may be provided, such as for example an articular insert, concave or convex, to be consequently coupled to the adjacent osseous element.

The other of the two stumps, called insertion stump, is shaped so as to be inserted in a corresponding seating made inside the bone on which the prosthetic element is applied.

According to a variant, in the case of arthrodesis, in other words, a fusion of the joint, the prosthetic element includes ogival elements that perform the function of the two stumps described above, to facilitate the insertion of the prosthetic element inside the bone part.

The trabecular part, which develops substantially central in the prosthetic element to define the external surface of the body or internal core, is formed by a lattice that defines open cavities that communicate with each other. The lattice is defined substantially by the repetition of a base cell the vertexes of which are not coplanar. For example, the base cell can be represented, in one solution, by the cubic crystalline structure of a diamond, or in any case, generally, by all those structures that can fill the space through repeating the cell.

In the case of a dental implant, the prosthetic element comprises both the insertion stump suitable for insertion of the prosthetic element inside the bone, and also the coupling stump, suitable for coupling with the dental prosthesis.

In this case, the coupling stump comprises a surface shaped for example like an embedded hexagon, that is, sunken.

According to a variant, the coupling stump comprises a surface shaped for example like an external hexagon, that is, in relief.

According to another non-restrictive variant, the hexagonal coupling is replaced by a conical coupling of the male or female type.

In the case of a dental implant, the coupling stump that couples with the dental prosthesis is made so as to guarantee solidity and clamping of the dental prosthesis, unlike what has to happen in the case of reconstruction of small joints, which have to guarantee the possibility of a correct movement, although of course within the right limits. Consequently, in the case of reconstruction of small joints, the coupling stump has a different profile from that of the coupling stump in the case of a dental implant.

In the case of reconstruction of small joints, the coupling stump comprises a concave or convex articular surface.

In the case of a dental implant, instead, the coupling stump comprises a surface with a profile like, for example, a Morse taper, with an embedded hexagon or external hexagon, for connection with the dental prosthesis.

Furthermore, the material that the prosthetic elements are made of in the case of reconstruction of small joints is normally titanium, its alloys or, alternatively, cobalt alloy. In dental prostheses, cobalt alloy is not normally used.

According to another characteristic of the present invention, the size of all the pores of the trabecular part is comprised in a range between 100 microns and 300 microns, with an average size comprised between 230 and 290 microns. These sizes are less than those correlated to the applications cited in the current state of the art, like for example those concerning prosthetic elements for knees and shoulders. In fact, in the case of the present invention, smaller bones are operated on, with different densities compared to what is described in the state of the art.

One of the techniques used to make the prosthetic elements according to the present invention is EBM (Electron Beam Melting), or DMSLS (Direct Metal Selective Laser Sintering) or SLM (Selective Laser Melting). Using this technique, a high energy source, consisting of a suitably concentrated and accelerated beam of electrons hits a material in powder form, in layers, causing it to melt completely and thus obtaining finished pieces without any empty spaces. The sequence of the layers obtains the three-dimensional piece, creating the stumps, core and trabecular part all at the same time, and allowing in this way to obtain structural and mechanical continuity of the various parts, which are in practice obtained in a single piece starting substantially from the working of a single material.

The layers of powder from which the prosthetic elements according to the present invention are made have a thickness of 50 microns, or in any case comprised between 20 microns and 70 microns.

There are two powders that can be used to make the prosthetic elements according to the present invention, that is, the standard one, with an average particle size of 70 microns, comprised between 45 microns and 100 microns, and a fine powder, comprised in a range from 25 to 45 microns. The latter gives better results compared with the particle size of standard powder, since a better working precision is obtained.

BRIEF DESCRIPTION OF THE DRAWINGS

These and other characteristics of the present invention will become apparent from the following description of one form of embodiment, given as a non-restrictive example with reference to the attached drawings wherein:

FIG. 1 is a lateral view of a prosthetic element according to the present invention, for a first application;

FIG. 2 is a longitudinal section of the prosthetic element in FIG. 1;

DETAILED DESCRIPTION OF ONE FORM OF EMBODIMENT

Figure 4:
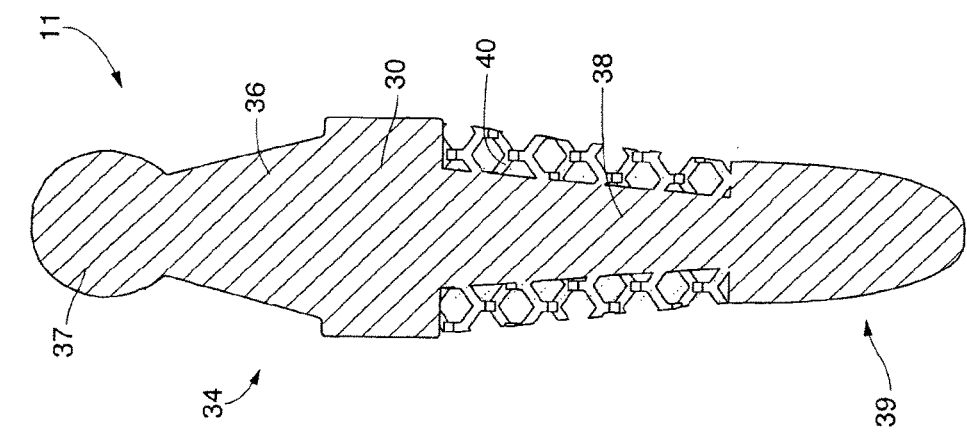
FIG. 4 is a longitudinal section of the prosthetic element in FIG. 3.

With reference to the drawings, a prosthetic element 10 (FIGS. 1 and 2) of a first type and a prosthetic element 11 (FIGS. 3, 4 and 5) of a second type, according to the present invention, are used for prosthetic implants suitable for bone extremities, for example in the case of reconstruction of small joints, like those of the fingers or toes. Furthermore, a prosthetic element 110 (FIGS. 6 and 7) of a third type is used according to the present invention for dental implants.

FIGS. 1 and 2 show a prosthetic element 10 suitable for use in the reconstruction of small joints. The prosthetic element 10 comprises a coupling stump 12, in turn comprising a lower surface 13 and an insertion ogive 15. The insertion ogive 15 in turn has an upper surface 16.

The coupling stump 12 and the insertion ogive 15 are joined together by an internal core 17, in this case consisting of a solid body with a truncated cone shape, having a structural function.

A trabecular part 20, with the function of bone integration, is made on the outside of the internal core 17 to be in contact on one side with the upper surface 16 of the insertion ogive 15, and on the other side with the lower surface of the coupling stump 12. The trabecular part 20, in this case, occupies a truncated cone bulk, except for the central part occupied by the internal core 17.

The trabecular part 20 is obtained in mechanical and structural continuity with respect to the internal core 17, using a technique chosen from those of EBM (Electron Beam Melting), or DMSLS (Direct Metal Selective Laser Sintering) or SLM (Selective Laser Melting), using substantially the same material and proceeding in sequential and progressive steps to form the finished structure.

In other words, the stump 12, ogive 15, core 17 and trabecular part 20 are structurally a single and continuous body, the geometry and form of which are made in a single production process, working the same material sequentially, for example using one or another of the techniques indicated above.

In this way great mechanical and structural resistance is guaranteed, and the maintenance over time of a structure that is unaltered both physically and mechanically, with great efficiency in terms of anchorage and osteo-integration.

In this case, the coupling stump 12 comprises a cylindrical part 23 shaped so as to have a semi-spherical cavity 25, suitable to couple, due to its shape and size, with a corresponding end of a second prosthetic element 11 (FIGS. 3 and 4), thus defining the joint to be reconstructed.

The insertion ogive 15 is configured, in shape and size, so as to be inserted in the bone part, not shown in the drawings, of the part to be operated on, such as for example the finger or toe, in order to reconstruct the joint.

Figure 3:
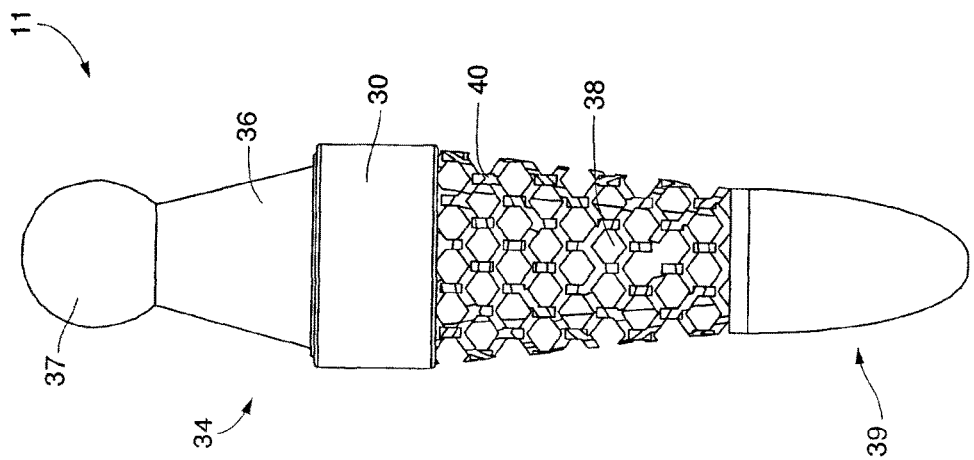
FIG. 3 is a lateral view of a complementary prosthetic element of the prosthetic element in FIG. 1.

In FIGS. 3 and 4, the prosthetic element 11 is substantially complementary to the prosthetic element 10 to obtain the reconstruction of a joint.

The prosthetic element 11 of the second type has substantially the same properties as the prosthetic element 10 of the first type, except for the conformation of the coupling stump. In fact, the prosthetic element 11 is provided with a coupling stump 34 shaped so as to make a conical part 36 and a spherical part 37, with a conformation such as to allow insertion inside the semi-spherical cavity 25, allowing the joint to move.

Furthermore, the prosthetic element 11 comprises an insertion ogive 39, configured in shape and size so as to be inserted inside the bone, a solid internal core 38 and a trabecular part 40 that constitutes the cover and coating in a single body of the internal core 38.

Figure 5:
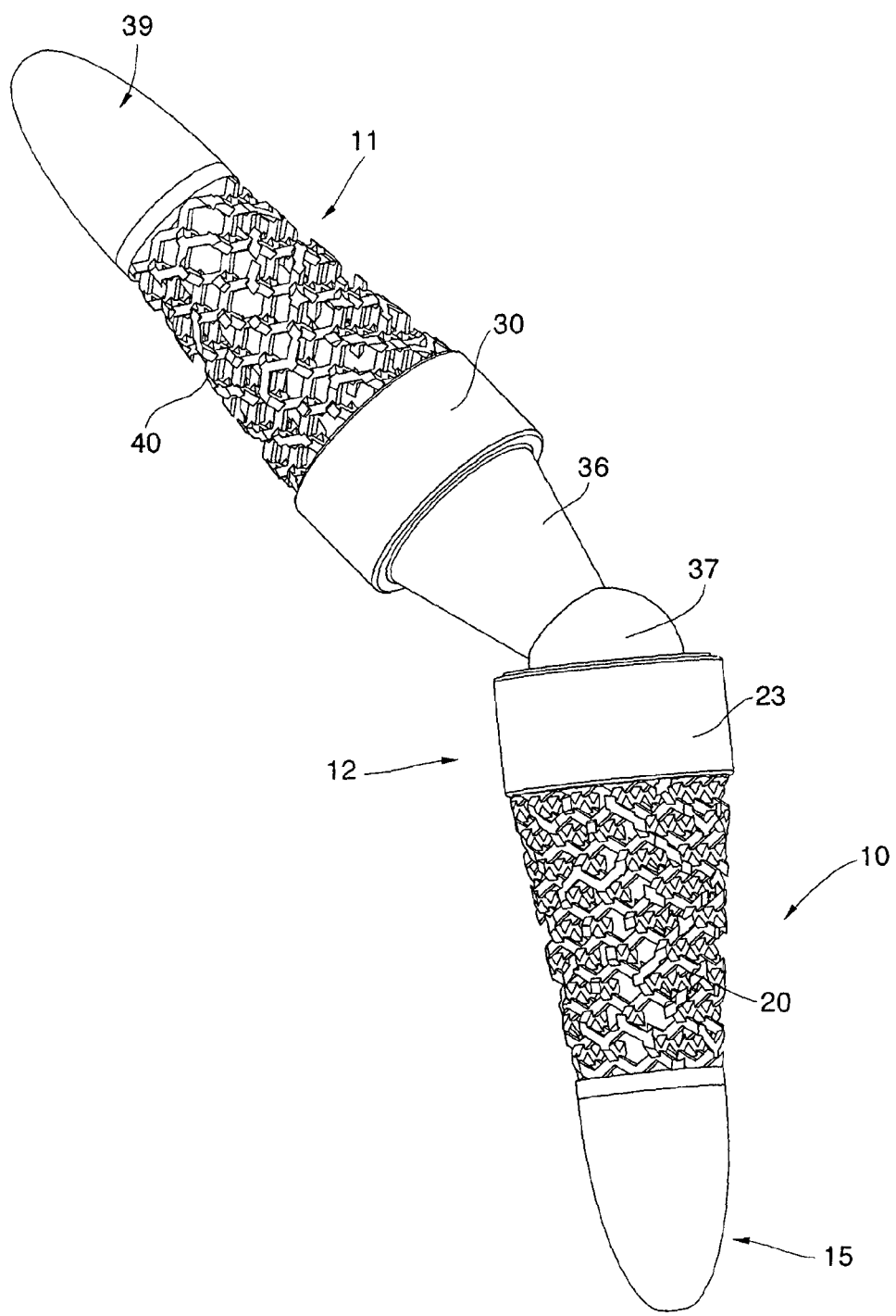
FIG. 5 is a three-dimensional view of the prosthetic element in FIG. 1 coupled with the prosthetic element in FIG. 3.

FIG. 5 shows the coupling of the prosthetic element 10 of the first type with the prosthetic element 11 of the second type, thus defining the joint to be reconstructed.

Figure 7:
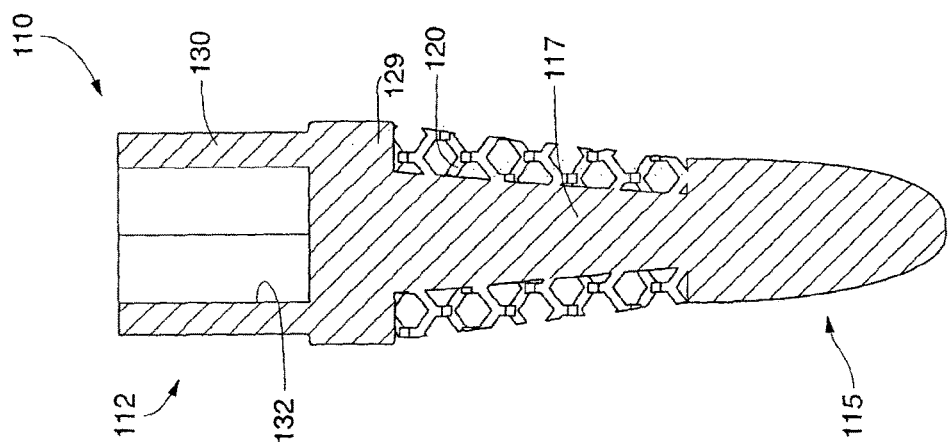
FIG. 7 is a longitudinal section of the prosthetic element in FIG. 6.
Figure 6:
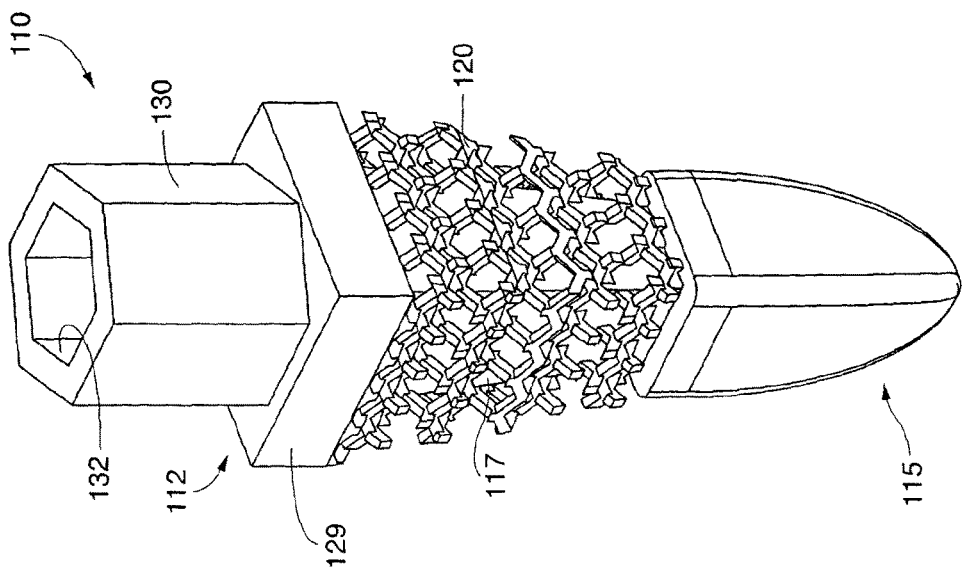
FIG. 6 is a three-dimensional view of a prosthetic element according to the present invention, for a second application.

In FIGS. 6 and 7, a prosthetic element 110 of a third type is suitable to be used for dental implants. In the same way as for the reconstruction of small joints, the prosthetic element 110 comprises a coupling stump 112 and an insertion stump 115. The coupling stump 112 in turn comprises a parallelepiped part 129 and a part with a hexagonal profile 130, and its function is to couple the prosthetic element 110 with a dental prosthesis, not shown in the drawings, which will be positioned above the prosthetic element 110. The part with a hexagonal profile 130 comprises a hexagonal cavity 132, suitable to keep the dental prosthesis clamped.

The part with a hexagonal profile 130 and the hexagonal cavity 132, exactly because of its shape, guarantee a secure clamping of the dental prosthesis.

A solid internal core 117 and a trabecular part 120 are disposed in the same way as those of the prosthetic element 10 in FIGS. 1 and 2; they also have the same properties and functions.

The processes for making the three types of prosthetic elements can also be the same, or in any case similar to those described above.

It is clear that modifications and/or additions of parts may be made to the prosthetic element 10, 11, 110 as described heretofore, without departing from the field and scope of the present invention.

It is also clear that, although the present invention has been described with reference to some specific examples, a person of skill in the art shall certainly be able to achieve many other equivalent forms of prosthetic element, having the characteristics as set forth in the claims and hence all coming within the field of protection defined thereby

The invention claimed is:

1. Prosthetic element for small bone extremities, comprising: a coupling stump disposed at a first end of said prosthetic element, an insertion stump disposed at a second end of the prosthetic element and shaped for insertion into a corresponding seating made inside the bone, a structural internal core comprising a solid body disposed intermediate between said stumps, and a trabecular part suitable for bone integration and disposed so as to cover and line said internal core to form in a single body a geometry external to said internal core and having mechanical and structural continuity with said internal core, wherein said coupling stump comprises a lower surface and said insertion stump comprises an upper surface, said trabecular part arranged to be in contact on said upper surface of said insertion stump and in contact with said lower surface of said coupling stump, and wherein said internal core, said insertion stump and said coupling stump comprise a single and continuous body.

2. Prosthetic element as in claim 1, wherein said coupling stump is configured in shape and size so as to define at least a seating for a joint of at least a finger or a toe.

3. Prosthetic element as in claim 1, wherein said coupling stump is configured in shape and size to couple with a dental prosthesis.

4. Prosthetic element as in claim 3, wherein said coupling stump comprises a shaped surface with a configuration chosen between an embedded hexagon shape, an external hexagon shape and a conical surface.

5. Prosthetic element as in claim 1, wherein said trabecular part comprises pores sized in a range between 100 microns and 300 microns and having an average size comprised between 230 microns and 290 microns.

6. Prosthetic element as in claim 5, wherein said trabecular part is defined at least in part by the repetition of a three-dimensional base cell the vertexes of which are not coplanar.

7. Method to make the prosthetic element of claim 1, the method comprising a fusion step, the fusion step comprising using either a beam of electrons, laser rays to simultaneously make the coupling stump, the insertion stump, the core, and the trabecular part to make a single body with structural and mechanical continuity, the method including using layers of material in a powder state and causing the fusion thereof, said layers of powder having a thickness comprised between 20 microns and 70 microns.

8. Method as in claim 7, wherein said powder with which said layers are made has a particle size comprised between 25 microns and 45 microns.

9. Method as in claim 7, wherein said powder with which said layers are made has a particle size comprised between 45 microns and 100 microns.

10. Prosthetic element for a bone extremity comprising:
a coupling stump disposed at a first end of the prosthetic element and being shaped to define a seating to permit articulation of the bone extremity, the coupling stump including a lower surface;
an insertion stump disposed at a second end of the prosthetic element, the insertion stump sized and shaped for insertion into a corresponding seating provided in the bone extremity, the coupling stump including an upper surface;
an internal core consisting of a solid body disposed intermediate between the coupling stump and the insertion stump, the solid body extending to the coupling stump adjacent the first end and to the insertion stump to adjacent the second end;
a trabecular part comprising a lattice structure arranged for bone integration, the trabecular part disposed about and surrounding the internal core, the trabecular part and the internal core forming a continuous integral structure;
the trabecular part couples to the lower surface of the coupling stump and to the upper surface of the insertion stump; and
wherein the internal core, the insertion stump, the coupling stump, and the trabecular part form a finished element obtained in a substantially continuous production step;
and further wherein the coupling stump, the insertion stump, the internal core, and the trabecular part are structurally a single and continuous body.

11. Prosthetic element as in claim 10, Wherein the insertion stump, the coupling stump, the trabecular part, and the core are all formed of the same base material.

* * * * *